(12) United States Patent
Daphna et al.

(10) Patent No.: US 11,678,973 B2
(45) Date of Patent: Jun. 20, 2023

(54) CORNEAL IMPLANT INJECTOR SYSTEM

(71) Applicant: EyeYon Medical Ltd., Nes Ziona (IL)

(72) Inventors: Ofer Daphna, Beit Elazari (IL); Dmitry Dubson, Rehovot (IL); Nahum Ferera, Petah Tikva (IL); Oriah Mioduser Cohen, Tel Aviv (IL); Elie Eliachar, Haifa (IL)

(73) Assignee: Eyeyon Medical Ltd., Nes Ziona (IL)

( * ) Notice: Subject to any disclaimer, the term of this patent is extended or adjusted under 35 U.S.C. 154(b) by 258 days.

(21) Appl. No.: 16/884,202

(22) Filed: May 27, 2020

(65) Prior Publication Data
US 2021/0369443 A1    Dec. 2, 2021

(51) Int. Cl.
*A61F 2/14*    (2006.01)

(52) U.S. Cl.
CPC .............. *A61F 2/148* (2013.01); *A61F 2/142* (2013.01)

(58) Field of Classification Search
CPC .. A61F 2/14; A61F 2/142; A61F 2/148; A61F 2/1662; A61F 2/167; A61F 2/1678; A61F 2/1691; A61F 9/0008; A61F 9/0017; A61F 9/0026; A61F 9/007
See application file for complete search history.

(56) References Cited

U.S. PATENT DOCUMENTS

| | | | |
|---|---|---|---|
| 8,403,941 B2 * | 3/2013 | Peterson | A61F 2/1691 606/107 |
| 8,475,526 B2 * | 7/2013 | Pynson | A61F 2/167 623/6.12 |
| 8,668,735 B2 * | 3/2014 | Nigam | A61F 2/148 606/107 |
| 10,105,258 B2 * | 10/2018 | Dockhom | A61F 2/1678 |
| 2003/0045930 A1 * | 3/2003 | Nguyen | A61F 2/16 606/107 |
| 2006/0235430 A1 * | 10/2006 | Le | A61F 2/148 606/107 |
| 2013/0023892 A1 * | 1/2013 | Schneider | A61F 2/142 606/107 |
| 2015/0238687 A1 * | 8/2015 | Novakovic | A61M 5/158 604/502 |
| 2015/0342730 A1 * | 12/2015 | Messner | A61F 2/167 606/107 |
| 2019/0224002 A1 * | 7/2019 | Springer | A61F 9/007 |
| 2020/0015958 A1 * | 1/2020 | Zacher | A61F 2/167 |
| 2020/0206029 A1 * | 7/2020 | Abdullayev | A61F 2/142 |

* cited by examiner

*Primary Examiner* — Sarah W Aleman
(74) *Attorney, Agent, or Firm* — Dekel Patent Ltd.; David Klein

(57) ABSTRACT

A corneal implant injector system includes an injector including a plunger slidable in a plunger housing, and a distal cartridge grabbing member engageable with an implant-holding cartridge.

9 Claims, 5 Drawing Sheets

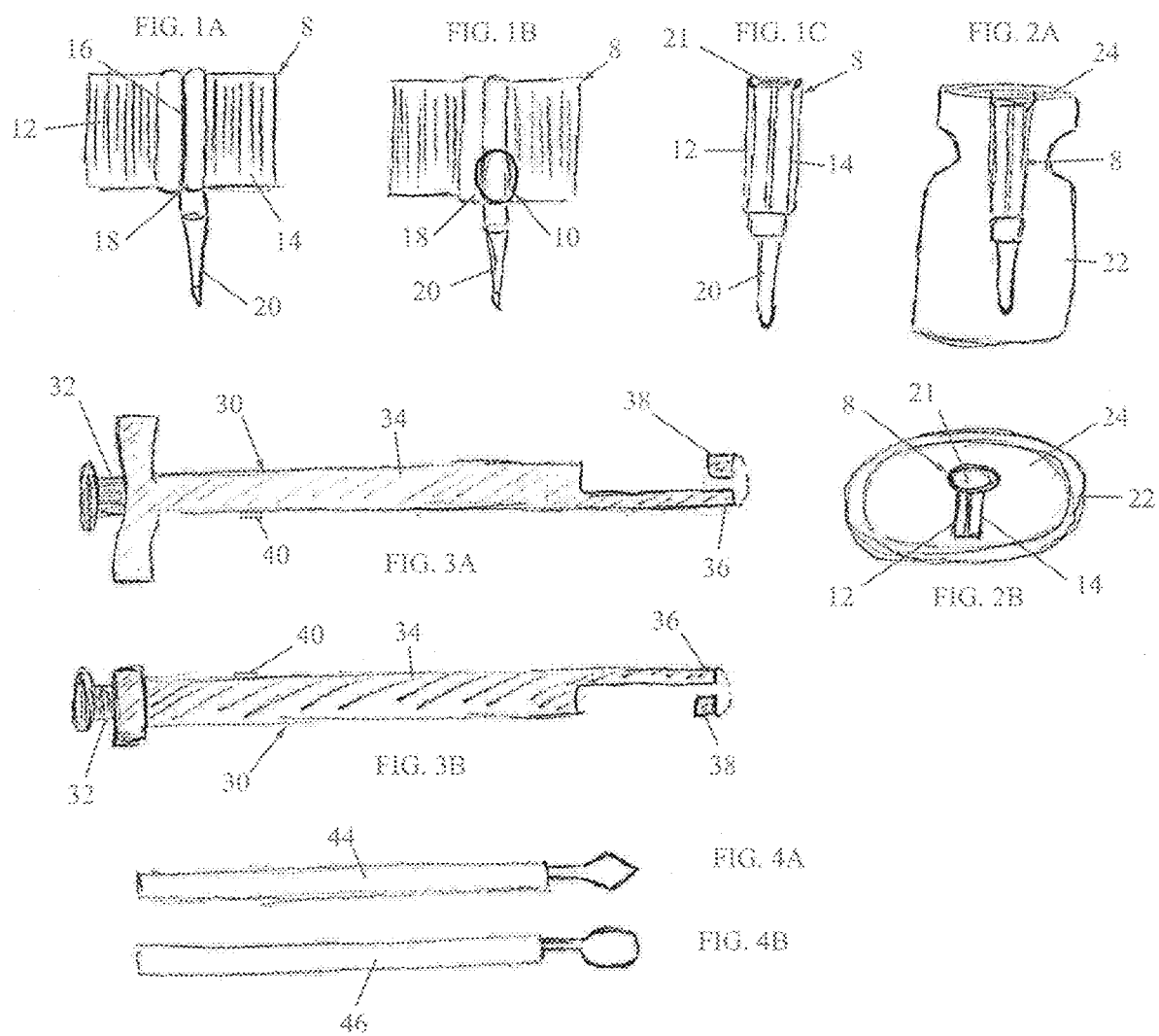

CORNEAL IMPLANT INJECTOR SYSTEM

FIELD OF THE INVENTION

The present invention relates generally to corneal implants, such as for treating an over-hydrated, edematous cornea, and particularly to an injector tool for injecting a corneal implant.

BACKGROUND OF THE INVENTION

U.S. Pat. Nos. 8,109,997 and 8,500,803 to Daphna describe a hydrophobic pseudo-endothelial implant, which is adhered to a posterior portion of the cornea adjacent the aqueous humor. The implant serves as a water barrier enabling dehydration of the cornea, and is used in the treatment of an edematous cornea.

The implant, which is typically about 3-10 mm in diameter, may be introduced through a small corneal incision of about 1-3 mm. The implant affixes to the posterior of the cornea without sutures or mechanical fasteners. Prior art IOL injectors are not well adapted for introducing the implant. Thus it is desirable to have an improved injector for this implant.

SUMMARY OF THE INVENTION

The present invention relates to an improved injector tool for injecting a corneal implant, as is described more in detail hereinbelow.

There is provided in accordance with an embodiment of the present invention a corneal implant injector system including an injector including a plunger slidable in a plunger housing, and a distal cartridge grabbing member engageable with an implant-holding cartridge.

The distal end of the plunger housing may include a sharp edge.

The cartridge grabbing member may include a pivotable clasp.

An actuator may be coupled to and operative to manipulate the cartridge grabbing member.

The corneal implant injector system may further include a cartridge and a corneal implant disposed therein, the cartridge having an aperture for the piston to pass therethrough and a cartridge outlet for the corneal implant to pass therethrough.

The cartridge may be disposed in a vial sealed by a puncturable septum.

BRIEF DESCRIPTION OF THE DRAWINGS

The present invention will be understood and appreciated more fully from the following detailed description taken in conjunction with the drawings in which:

FIGS. 1A, 1B and 1C are simplified pictorial illustrations of a cartridge for holding a corneal implant, constructed and operative in accordance with a non-limiting embodiment of the present invention, respectively, in an open configuration without the implant, in an open configuration with the implant, and in a closed configuration with the implant;

FIGS. 2A and 2B are simplified pictorial illustrations of the closed and loaded cartridge placed in a vial;

FIGS. 3A and 3B are simplified pictorial illustrations of an injector, constructed and operative in accordance with a non-limiting embodiment of the present invention;

FIGS. 4A and 4B are simplified pictorial illustrations of other tools which may be used in the process of introducing the implant into the eye, such as a knife or keratome (FIG. 4A) and a spreading tool (FIG. 4B);

DETAILED DESCRIPTION OF EMBODIMENTS

Figure 5A:
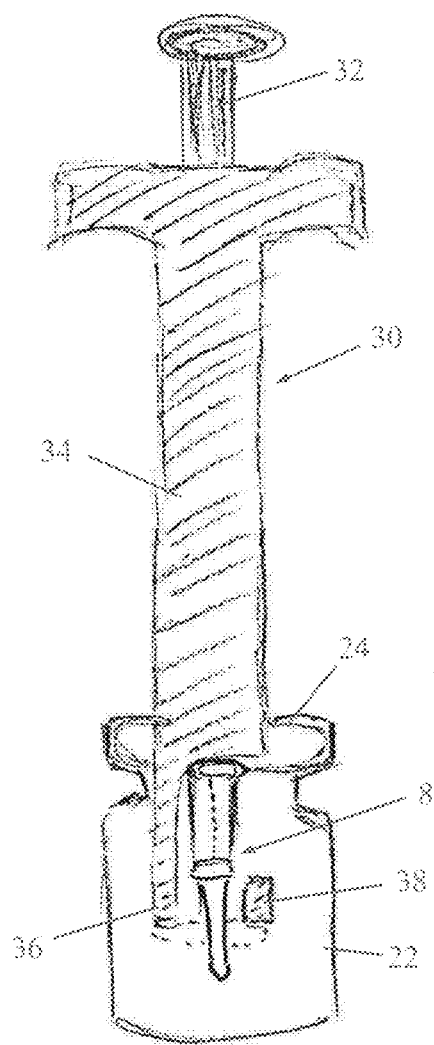
FIGS. 5A and 5B are simplified pictorial illustrations of the injector being used to grasp the cartridge.

Reference is now made to FIGS. 1A, 1B and 1C, which illustrate a cartridge 8 for holding a corneal implant 10, constructed and operative in accordance with an embodiment of the present invention.

The implant 10 may be a hydrophobic pseudo-endothelial implant, such as the ENDOART implant available from Eyeyon Medical Ltd., Israel.

Cartridge 8 may include first and second housing halves 12 and 14, which may be pivotally coupled to one another about a hinge 16. Cartridge 8 may include an implant receiving portion 18, such as but not necessarily, at or near hinge 16. As seen in FIG. 1B, the implant 10 may be placed in implant receiving portion 18, and then first and second housing halves 12 and 14 are closed as in FIG. 1C. When closed in the cartridge 8, the implant 10 is curled or folded. Cartridge 8 may include a cartridge outlet 20, which is preferably tapered so that the implant 10 exits the cartridge 8 with a minimal perimeter for insertion through a small corneal incision of about 3-4 mm, without limitation. The top of the closed cartridge 8 (that is, the end opposite to cartridge outlet 20) may have an aperture 21. This allows access to push the implant 10 out of the cartridge 8.

Reference is now made to FIGS. 2A and 2B, which illustrate the closed and loaded cartridge 8 placed in a vial 22. Vial 22 may be sealed by a puncturable septum 24. Depending on the application and need, vial 22 may contain a viscoelastic fluid, such as 0.9% saline, or 1% sodium hyaluronate solution.

Reference is now made to FIGS. 3A and 3B, which illustrate an injector 30, constructed and operative in accordance with an embodiment of the present invention. Injector 30 includes a plunger 32 which slides in a plunger housing 34. A distal end of plunger housing 34 includes an elongated cannula, or a sharp edge 36. In addition, injector 30 includes a distal cartridge grabbing member 38. In one non-limiting example, the cartridge grabbing member 38 includes a pivotable clasp which can be manipulated by an actuator 40, such as a pushable or turnable knob coupled to cartridge grabbing member 38. As another example, cartridge grabbing member 38 does not have to be pivotable, but instead includes resilient tabs which click onto a portion of the cartridge. As yet another alternative, cartridge grabbing member 38 may be notches or recesses into which a portion of the cartridge is received. As yet another alternative, cartridge grabbing member 38 may be a magnetic member which adheres by magnetic attraction to a magnetized portion of the cartridge.

Reference is now made to FIGS. 4A and 4B, which illustrate other tools which may be used in the process of introducing the implant into the eye, such as a knife or keratome 44 (FIG. 4A) and a spreading tool 46 (FIG. 4B). It is contemplated to have one or both of these tools incorporated in the injector 30, so that injector 30 is a multi-purpose tool.

Figure 5B:
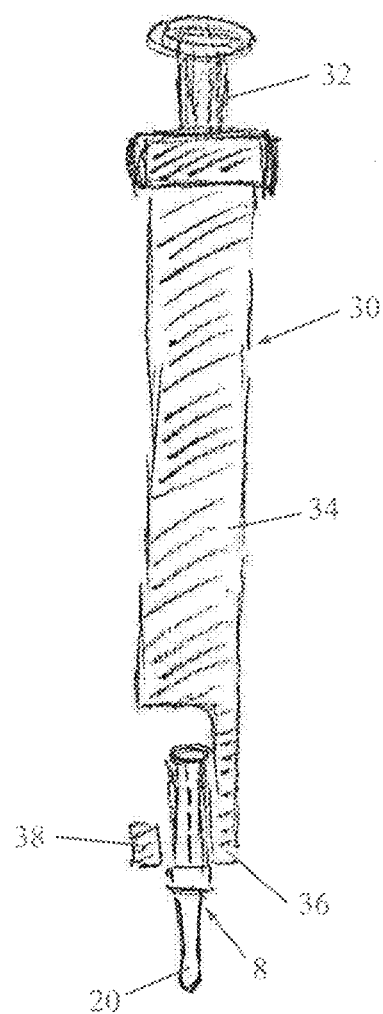

Reference is now made to FIGS. 5A and 5B, which illustrate use of the injector 30 to grasp the cartridge 8. The sharp edge 36 of the distal end of plunger housing 34 of injector 30 is used to puncture the septum 24 of vial 22. The cartridge grabbing member 38 grabs cartridge 8.

Reference is now made to FIGS. 6A-6D, which illustrate use of the injector 30 to introduce the implant 10 into the eye.

Figure 6A:
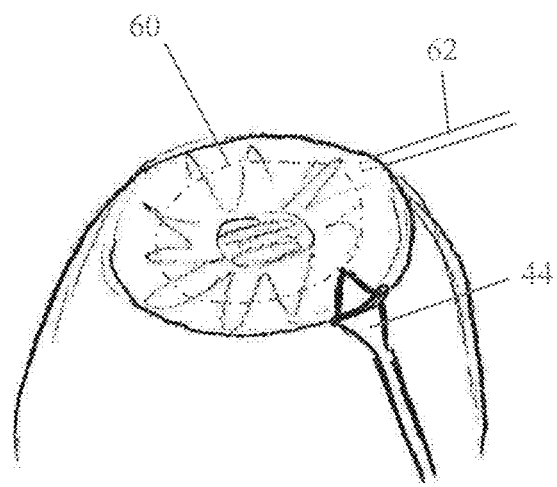
FIGS. 6A-6D are simplified pictorial illustrations of use of the injector to introduce the implant into the eye, in accordance with a non-limiting embodiment of the present invention.

In FIG. 6A, the cornea may be first marked with a mark 60, made by a circular marker (not shown), as is known in the art. A maintainer 62 may be introduced through a very small incision (e.g., less than 2 mm) near the limbus. As is known in the art, the maintainer 62 may be first soaked for a few minutes in fortified balanced salt solution (BSS) or modified Ringer's solution. Knife 44 makes a small corneal incision of about 1-3 mm, without limitation, such as near the limbus. (For simplicity, mark 60 and maintainer 62 are only shown in FIG. 6A.)

Figure 6B:
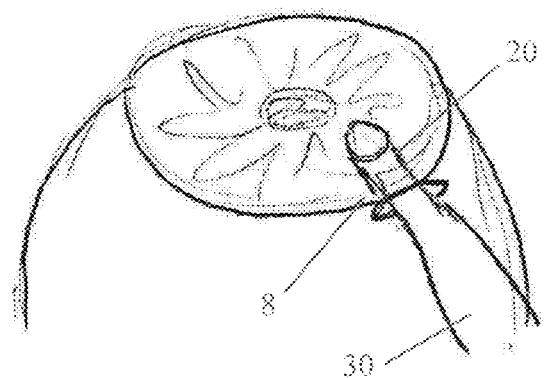

In FIG. 6B, the cartridge outlet 20 of cartridge 8 is inserted through the small corneal incision by the injector 30.

Figure 6C:
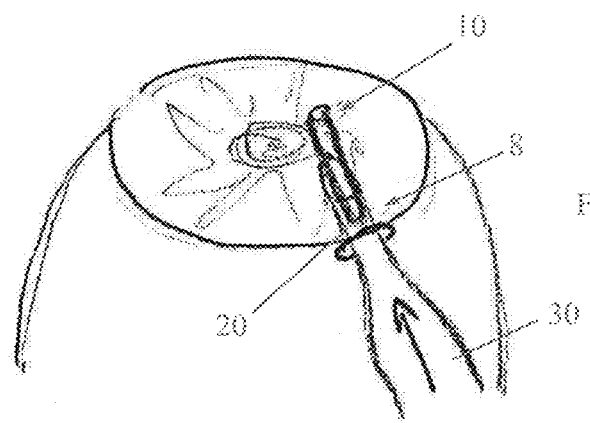

In FIG. 6C, the plunger of the injector 30 pushes the implant 10 out of the cartridge outlet 20 of cartridge 8 into the corneal space.

Figure 6D:
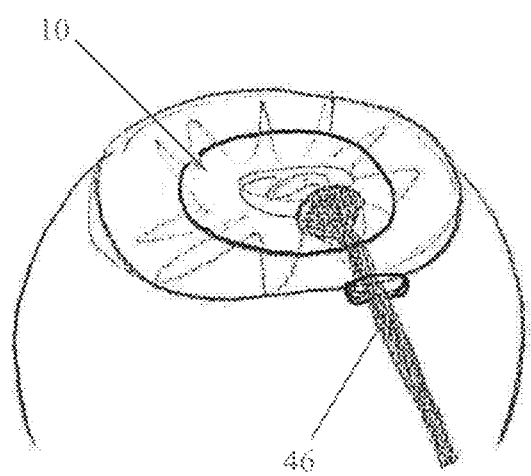

In FIG. 6D, spreading tool 46 is inserted through the small corneal incision to spread and position the implant 10. As is known in the art, an air bubble may be introduced into the corneal space to help position and center the implant 10.

Prior to bonding implant 10 to the posterior portion of the cornea, as in PLK (posterior lamellar keratoplasty) or DSEK (Descemet's stripping endothelial keratoplasty), a thin posterior or lenticule of stromal tissue (along with Descemet's membrane and endothelial cells attached) may be removed from the cornea of the patient's eye. Alternatively, as in Descemet's strip endokeratoplasty, only the Descemet's membrane and endothelial cells are removed. Alternatively, the implant 10 may be attached to the endothelium of the cornea without any posterior surface stripping.

Figure 7A:
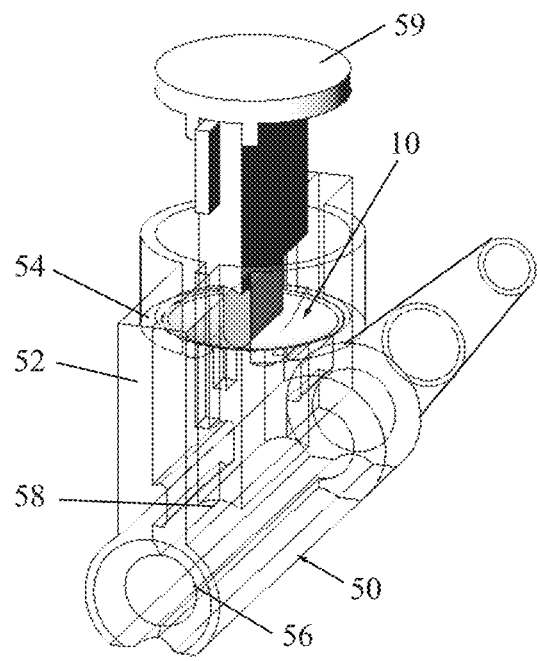
FIGS. 7A and 7B are simplified illustrations of a cartridge for holding a corneal implant, constructed and operative in accordance with a non-limiting embodiment of the present invention, respectively before and after folding the implant into the cartridge.
Figure 7B:
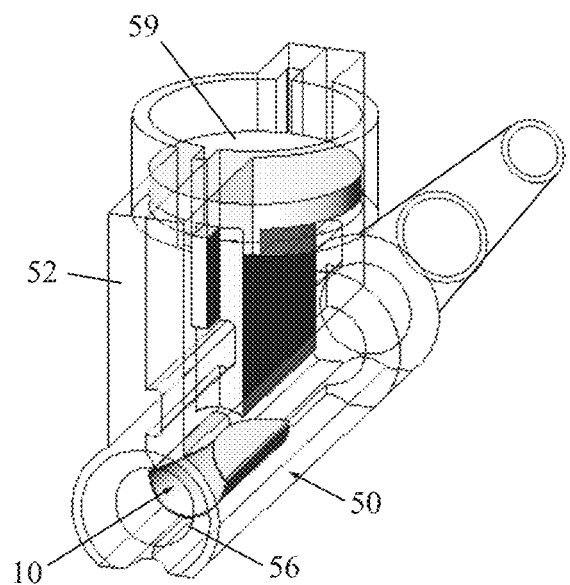

Introduction of the implant into the cartridge may be accomplished in different ways. Reference is now made to FIGS. 7A and 7B, which illustrate one non-limiting exemplary way of introducing the implant into the cartridge.

In FIG. 7A, a cartridge 50 is provided for holding implant 10. The cartridge 50 may be coupled to an implant pusher member 52, which has an implant mounting portion 54, in which the implant 10 may be placed in an unfolded position. The cartridge 50 has an implant receiving portion 56. The cartridge 50 may be formed with an elongate aperture (e.g., slit) 58 through which the implant 10 may be pushed from the implant mounting portion 54 to the implant receiving portion 56. The implant pusher member 52 is shown in FIG. 7A as being perpendicular to the implant receiving portion 56, but it is appreciated that in other embodiments, the implant pusher member 52 may be in-line with the implant receiving portion 56 or oriented at other angles. The implant pusher member 52 includes a pusher 59 that pushes the implant 10 from the implant mounting portion 54 through elongate aperture 58 into the implant receiving portion 56 (as seen in FIG. 7B). After being pushed into the implant receiving portion 56, the implant 10 may have a folded or curled orientation, as seen in FIG. 7B.

Figure 7C:
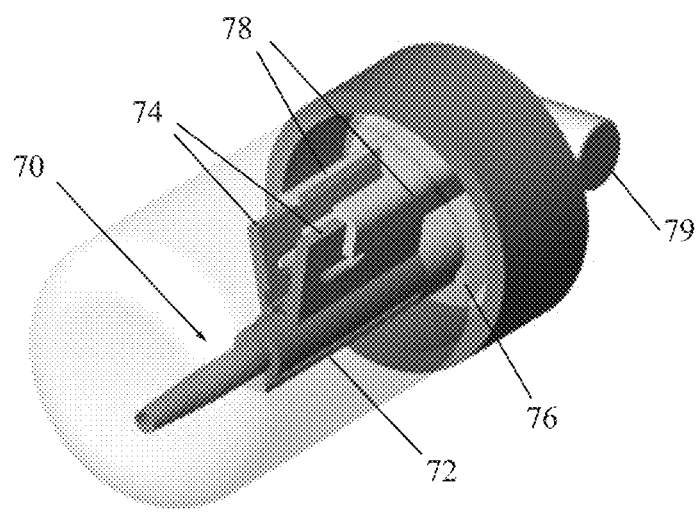
FIG. 7C is a simplified illustration of a cartridge for holding a corneal implant, constructed and operative in accordance with another non-limiting embodiment of the present invention, shown after folding the implant into the cartridge.

Reference is now made to FIG. 7C, which illustrates a cartridge 70 for holding the corneal implant, constructed and operative in accordance with another non-limiting embodiment of the present invention, shown after folding the implant (not seen) into cartridge 70.

The cartridge 70 may include a foldable implant receiving portion 72, which includes two extensions 74. Cartridge 70 may be coupled to an implant pusher member 76, which may be in-line with the implant receiving portion 72. The implant pusher member 76 includes coupling members 78 that engage the extensions 74; upon engagement and pushing, the coupling members 78 fold the extensions 74 so that the implant is in a folded configuration inside cartridge 70. The implant pusher member 76 may be constructed as a piston with a pushing handle 79.

What is claimed is:

1. A corneal implant injector system comprising:
   an injector comprising a plunger slidable in a plunger housing;
   a distal cartridge grabbing member engageable with an implant-holding cartridge; and
   a cartridge and a corneal implant disposed therein, said cartridge having an aperture for said plunger to pass therethrough and a cartridge outlet for said corneal implant to pass therethrough;
   wherein said cartridge comprises first and second housing halves pivotally coupled to one another about a hinge, said cartridge comprising an implant receiving portion, and when said first and second housing halves are closed, said corneal implant is curled or folded in said implant receiving portion; and
   an implant pusher member coupled to said cartridge, said implant pusher member comprising:
   an implant mounting portion that has an annular rim with a central opening, said corneal implant being supported in an unfolded position on said annular rim:
   wherein said central opening extends to a slit formed along a longitudinal axis of said cartilage, said elongate aperture extending into said implant receiving portion; and
   a pusher slidable in said implant mounting portion and arranged to push said corneal implant from said annular rim through said central opening, through said slit and into said implant receiving portion, and wherein said corneal implant becomes folded or curled when passing through said elongate aperture.

2. The corneal implant injector system according to claim 1, wherein a distal end of said plunger housing comprises an elongated cannula or a sharp edge.

3. The corneal implant injector system according to claim 1, wherein said implant receiving portion is at or near said hinge.

4. The corneal implant injector system according to claim 1, further comprising an actuator coupled to and operative to manipulate said cartridge grabbing member.

5. The corneal implant injector system according to claim 1, wherein said cartridge outlet is tapered.

6. The corneal implant injector system according to claim 5, wherein said cartridge is disposed in a vial sealed by a puncturable septum.

7. The corneal implant injector system according to claim 1, wherein said implant pusher member is perpendicular to said implant receiving portion.

8. The corneal implant injector system according to claim 1, wherein said pusher comprises an enlarged head that is arranged to abut against said annular rim at an end of travel of said pusher.

9. The corneal implant injector system according to claim 1, wherein said implant receiving portion is foldable.

\* \* \* \* \*